(12) United States Patent
Cha et al.

(10) Patent No.: US 7,975,691 B2
(45) Date of Patent: Jul. 12, 2011

(54) CONTINUOUS POSITIVE AIRWAY PRESSURE DEVICE BY CONTROLLING THE PRESSURE IN THE FACE MASK

(76) Inventors: Eun Jong Cha, Cheongju (KR); Kyung Ah Kim, Cheongju (KR); Seong Sik Kim, Gunpo (KR); Seung Bum Kang, Cheongju (KR)

( * ) Notice: Subject to any disclaimer, the term of this patent is extended or adjusted under 35 U.S.C. 154(b) by 805 days.

(21) Appl. No.: 11/877,435

(22) Filed: Oct. 23, 2007

(65) Prior Publication Data

US 2009/0101148 A1    Apr. 23, 2009

(51) Int. Cl.
*A61M 11/00*    (2006.01)
(52) U.S. Cl. ............... 128/204.22; 128/204.18
(58) Field of Classification Search ............ 128/204.18, 128/204.21–204.23, 204.26, 204.29
See application file for complete search history.

(56) References Cited

U.S. PATENT DOCUMENTS

| | | | |
|---|---|---|---|
| 6,279,569 B1 * | 8/2001 | Berthon-Jones | 128/200.24 |
| 6,629,527 B1 * | 10/2003 | Estes et al. | 128/204.18 |
| 7,337,778 B2 * | 3/2008 | Martin et al. | 128/204.21 |
| 7,533,670 B1 * | 5/2009 | Freitag et al. | 128/204.23 |

* cited by examiner

*Primary Examiner* — Steven O Douglas
(74) *Attorney, Agent, or Firm* — Greer, Burns & Crain, Ltd.

(57) ABSTRACT

A CPAP device includes an air stream generator for generating positive pressure, a face mask connected to the air stream generator through a flow supply catheter, a pressure sensor measuring pressure in the face mask, a control circuit controlling the air stream generator, and a pressure detection pipe having a first side and a second side. The pressure sensor is connected to the second side of the pressure detection pipe to measure pressure of the detection hole formed at the first side of the pressure detection pipe and outputs the measured pressure value to the control circuit. The control circuit distinguishes average positive pressure from pressure caused by spontaneous breathing of patient according to values of the pressure in the face mask, which are input from the pressure sensor, and controls a speed of the air stream generator such that preset positive pressure is supplied to the patient.

4 Claims, 3 Drawing Sheets

CONTINUOUS POSITIVE AIRWAY PRESSURE DEVICE BY CONTROLLING THE PRESSURE IN THE FACE MASK

BACKGROUND OF THE INVENTION

1. Field of the Invention

The present invention relates to a CPAP (continuous positive airway pressure) device controlling pressure in a face mask. More particularly, the present invention relates to a device for supplying proper positive pressure by using a structure precisely measuring the breathing state of a patient.

2. Description of the Related Art

In general, when a person sleeps, all the muscles in the body of the person are relaxed. In addition to muscles of the trachea, muscles of the uvula or the throat are also relaxed, so the diameter of the trachea is reduced. Even if the diameter of the trachea is slightly reduced during sleeping, most persons feel no difficulty in breathing. However, some persons snore when breathing in due to the narrowed trachea or experience sleep apnea.

When the sleep apnea continues, the arterial oxygen saturation is excessively reduced, so circulatory disease such as hipertension, arrhythmia, ischemic heard disease, heart failure or cerebral palsy may easily occur. Further, the sleep apnea may cause insulin insufficiency, which is the main factor of diabetes, or may cause pulmonary disease/heart disease to become worse. In addition, the sleep apnea may cause sudden death during sleeping. According to statistics, a sleep apnea patient has a high incidence rate of hypertenstion (about twice as compared with that of ordinary people), arrhythmia (about twice as compared with that of ordinary people), coronary heart disease (about three times as compared with that of ordinary people), cerebrovascular (about four times as compared with that of ordinary people), and traffic accidents (about three times to about seven times as compared with that of ordinary people).

A CPAP therapy is representatively used for curing such a sleep apnea. According to the CPAP therapy, air having pressure is continuously supplied to the throat of a patient through a mask making closely contact with the nose of the patient during sleeping, so that the airway of the patient can be prevented from being obstructed. A positive airway pressure ventilator aids such a therapy. That is, the positive airway pressure ventilator supplies positive pressure air to a snoring or sleep apnea patient through a mask, who wears the mask on the nose during sleeping, thereby aiding the patient to easily breathe and thus curing the sleep apnea. This is the most secure and effective method of the non-surgical methods.

As shown in FIG. 6, a conventional CPAP device performing the functions as described above has a structure in which two pressure sensors are installed at the end portion of a flow supply catheter connected to a face mask while interposing a fluid resistor therebetween.

Referring to FIG. 6, since $P_2$ reflects pressure in the flow supply catheter, an air stream generator is controlled to obtain a desired pressure value. At this time, an object, which must be substantially controlled, is pressure supplied to a patient, i.e. pressure $P_m$ in the face mask. However, a scheme of controlling the air stream generator by using signals $P_1$ and $P_2$ has been employed on the assumption that the fluid resistor of the flow supply catheter is very low (Rc≈0) or $P_m$ can be estimated from $P_2$.

This is because it is inconvenient to install the pressure sensors, and the flow supply catheter and electric wire, which interconnect with the pressure sensors, around the face mask worn by a patient.

In order to estimate $P_m$ from the pressure sensor $P_2$, one fluid resistor R and one pressure sensor $P_1$ must be additionally used. Accordingly, the air stream F supplied to the face mask is measured to estimate $P_m$. That is, since the fluid resistor is installed between $P_1$ and $P_2$, the air stream F has a value expressed by Equation 1 below.

$$F = \frac{P_1 - P_2}{R} \quad \text{Equation 1}$$

When the fluid resistance of the flow supply catheter for air stream supply, which is connected to the face mask, is $R_c$, Equation 2 below is established.

$$F = \frac{P_2 - P_m}{R_c} \quad \text{Equation 2}$$

Equation 3 below is established from Equations 1 and 2.

$$P_m = \left(1 + \frac{R_c}{R}\right)P_2 - \frac{R_c}{R}P_1 \quad \text{Equation 3}$$

Accordingly, $P_m$ can be estimated from $P_1$ and $P_2$. At this time, if $R_c$ has a value of 0, $P_m$ becomes equal to $P_2$. However, since the fluid resistance of the flow supply catheter is always larger than 0, $P_2 > P_m$. Thus, $P_m$ cannot be estimated before $P_1$ and $P_2$ are measured.

The conventional CPAP device as described above has the following problems.

First, two pressure values must be measured to generate air stream such that $P_m$ has a constant value (positive pressure) through Equation 3. Since $P_1$ and $P_2$ are essentially changed according to the generated air stream, the number (i.e. two) of control parameters is increased, causing the waste of circuit sources.

Second, providing that $R_c$ has a value of 0 in Equation 3, $P_2$ becomes equal to $P_m$ and only $P_2$ is controlled. However, since the fluid resistance of the flow supply catheter is always larger than 0, the control cannot be exactly performed.

Third, since the CPAP device is a medical instrument for preventing a patient from dying due to the sleep apnea during sleeping, it must be monitored whether the patient is spontaneously breathing. This can be achieved by detecting oscillation of pressure $P_m$ in the face mask, which is caused by spontaneous breathing of the patient, on the basis of a target control value. In such a case, since $P_2$ cooperates with $P_m$, a method of determining if the patient is spontaneously breathing by detecting the oscillation of $P_2$ is used. However, since the flow supply catheter has a long length (>70 cm) and $R_c \neq 0$, $P_2$ is less oscillated as compared with $P_m$. Thus, an error may occur in the breath detecting function.

Last, since two pressure sensors and one fluid resistor are used, the manufacturing cost is expensive.

SUMMARY OF THE INVENTION

The present invention has been made to solve the above problems occurring in the prior art, and an object of the present invention is to provide an apparatus for precisely detecting and controlling the breath of a patient by directly measuring pressure in the face mask of a CPAP device.

Another object of the present invention is to provide a structure precisely measuring the breath of a patient by directly measuring pressure in the face mask of a CPAP device, and an apparatus with the low manufacturing cost by reducing the number of elements used for the measurement.

In order to accomplish the above object, the present invention provides a CPAP device comprising: an air stream generator for generating positive pressure; a face mask connected to the air stream generator through a flow supply catheter; a pressure sensor measuring pressure in the face mask; a control circuit controlling the air stream generator; and a pressure detection pipe having a first side and a second side, the first side being installed such that a detection hole is located at a connection portion between the face mask and the flow supply catheter in order to directly measure pressure in the face mask, and the second side being connected to the pressure sensor through a through hole formed in the flow supply catheter, wherein the pressure sensor is connected to the second side of the pressure detection pipe to measure pressure of the detection hole formed at the first side of the pressure detection pipe and outputs the measured pressure value to the control circuit, the control circuit distinguishes average positive pressure from pressure caused by spontaneous breathing of patient according to values of the pressure in the face mask, which are input from the pressure sensor, and controls a speed of the air stream generator such that preset positive pressure is supplied to the patient, and the air stream generator generates air stream such that the pressure in the face mask maintains proper positive pressure under a control of the control circuit.

The pressure detection pipe has a diameter smaller than a diameter of the flow supply catheter, an end portion of the pressure detection pipe adjacent to the face mask is sealed, the detection hole is formed in the pressure detection pipe vertically to air stream, and the pressure detection pipe is selectively fixed to a wall of the flow supply catheter or not.

When the pressure detection pipe is not fixed to the wall of the flow supply catheter, at least two detection holes are formed vertically to the air stream, and a peripheral pressure value, which is physically averaged, is measured in the pressure detection pipe.

Further, when N detection holes are formed, an angle between two adjacent detection holes about a central axis of the pressure detection pipe is 360°/N when viewed in a sectional view.

The control circuit controls the pressure in the face mask to a desired level by using a signal, which has a frequency lower than a breathing frequency and is obtained by low-pass filtering a continuous signal of the pressure measured by the pressure-sensor, and detects only a breathing signal by high-pass filtering the continuous signal using a signal having a frequency higher than the breathing frequency.

BRIEF DESCRIPTION OF THE DRAWINGS

The above and other advantages of the present invention will become readily apparent with reference to the following detailed description when considered in conjunction with the accompanying drawings wherein.

DESCRIPTION OF THE EMBODIMENT

Hereinafter, a preferred embodiment of the present invention will be explained in detail with reference to the accompanying drawings.

Figure 1:
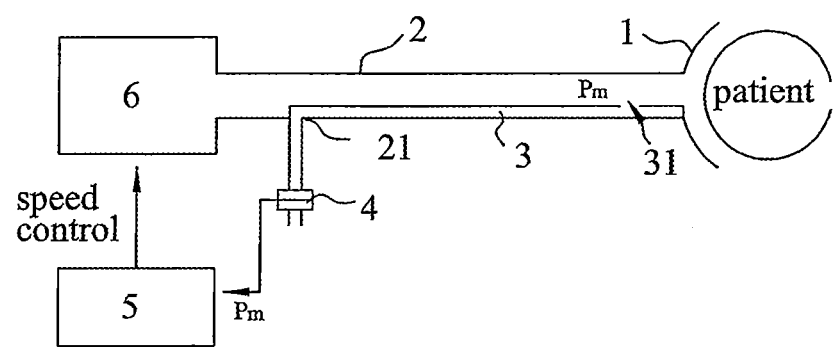
FIG. 1 is a block diagram schematically showing the construction of a CPAP device according to the present invention.

FIG. 1 is a block diagram schematically showing the construction of a CPAP device according to the present invention. As shown in FIG. 1, the CPAP device comprises a pressure detection pipe 3, a pressure sensor 4, a control circuit 5 and an air stream generator 6. The pressure detection pipe 3 has one side, which is installed such that a detection hole 31 is located at a connection portion between a face mask 1 and a flow supply catheter 2 in order to directly measure pressure $P_m$ in the face mask 1. Further, the pressure detection pipe 3 has the other side connected to the pressure sensor 4 through a through hole 21 formed in the flow supply catheter 2. The pressure sensor 4 is connected to the other side of the pressure detection pipe 3 to measure the pressure of the detection hole 31 formed at the first side of the pressure detection pipe, and outputs the measure pressure value to the control circuit 5. The control circuit 5 distinguishes average positive pressure from pressure caused by the spontaneous breathing of a patient according to values of the pressure $P_m$ in the face mask 1, which are input from the pressure sensor 4, and controls the speed of the air stream generator 6 such that preset positive pressure can be supplied to the patient. The air stream generator 6 generates air stream such that the pressure $P_m$ in the face mask 1 can maintain proper positive pressure under the control of the control circuit 5.

Figure 2:
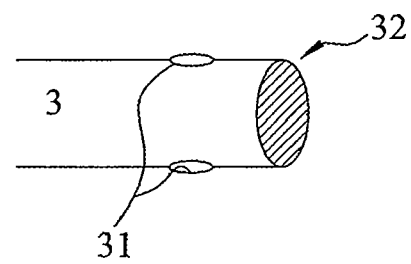
FIG. 2 is a view showing the structure of a pressure detection pipe according to the present invention.
Figure 3:
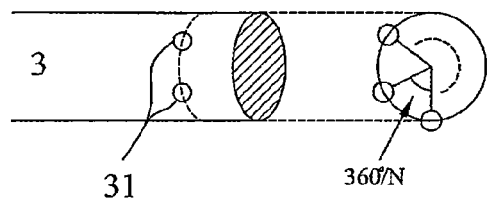
FIG. 3 is a view showing an angle between at least two detection holes formed in a pressure detection pipe according to the present invention.

FIG. 2 is a view showing the structure of the pressure detection pipe according to the present invention and FIG. 3 is a view showing an angle between at least two detection holes formed in the pressure detection pipe according to the present invention. The pressure detection pipe 3 may also be installed at the wall of the flow supply catheter for supplying air stream. However, the installation positions of the pressure detection pipe 3 have no relation to the operation of the device. Since lateral pressure must be measured in the direction vertical to the air stream, the end portion 32 of the pressure detection pipe 3 is sealed and the detection hole 31 must be formed in the lateral side of the pressure detection pipe 3. In consideration of a case in which the position of the pressure detection pipe 3 is not fixed, two or more detection holes are formed in the outer circumferential surface of the pressure detection pipe 3. Further, in the case of installing two detection holes as shown in FIG. 3, an angle between two adjacent detection holes about a central axis of the pressure detection pipe 3 is 180° when viewed in a sectional view. In the case of installing three detection holes, an angle between two adjacent detection holes about a central axis of the pressure detection pipe 3 is 120° when viewed in a sectional view.

That is, when N detection holes are formed, an angle between two adjacent holes about a central axis of the pressure detection pipe 3 is 360°/N when viewed in a sectional view.

Figure 4:
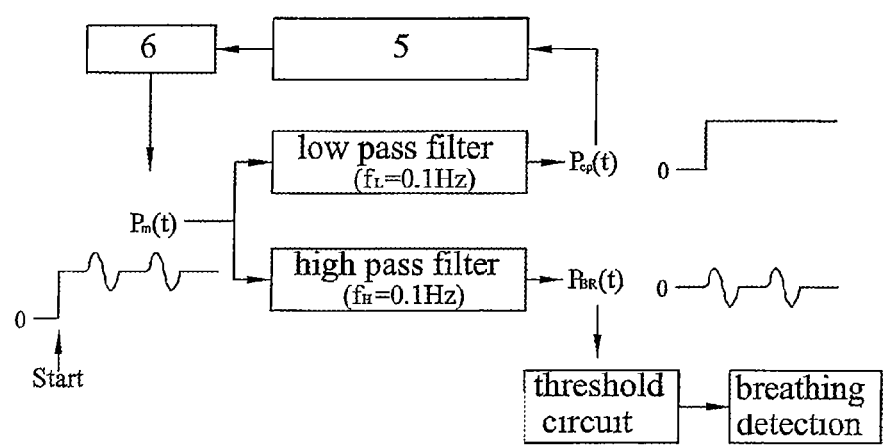
FIG. 4 is a block diagram showing the control flow of a control circuit according to the present invention.

FIG. 4 is a block diagram showing the control flow of the control circuit of the present invention. According to the present invention, the pressure $P_m$ oscillated by the spontaneous breathing of a patient is directly measured, so that the breathing state of the patient can be easily detected. To this end, there is provided a technique, in which the pressure in the face mask is controlled to a desired level by using a signal, which has a frequency lower than a breathing frequency and is obtained by low-pass filtering the continuous signal of the pressure $P_m$ measured by the pressure sensor, and then only a breathing signal is detected by high-pass filtering the continuous signal using a signal having a frequency higher than the breathing frequency. Since positive pressure is constantly maintained, the positive pressure corresponds to a signal similar to direct current having a frequency of 0. However, since the breathing frequency is about 0.2 Hz, a blocking frequency is set to 0.1 Hz, so that only the oscillation component of the pressure $P_m$ can be extracted.

In detail, $P_m(t)=P_{cp}(t)+P_{BR}(t)$. $P_{cp}(t)$ denotes the average positive pressure component of $P_m(t)$ constantly maintained, and $P_{BR}(t)$ denotes the oscillation component of $P_m(t)$ caused by the spontaneous breathing. $P_m$ Measured by the pressure sensor is obtained by sum of the two signal components.

Accordingly, $P_{cp}(t)$ filtered through the low pass filter can be used as a signal for controlling the average positive pressure supplied to a patient through the face mask by controlling the air stream generator. $P_{BR}(t)$ filtered through the high pass filter can be used for detecting the spontaneous breathing time point after passing through a threshold circuit. That is, the pressure signal before the face mask is directly measured, so that average positive pressure can be maintained and simultaneously whether or not a patient is breathing can be exactly determined.

In addition, according to the circuit having the construction as described above, only one pressure sensor is used, so that the manufacturing cost can be significantly reduced.

Figure 5:
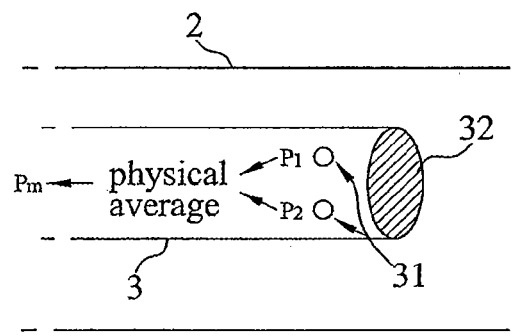
FIG. 5 is a view showing a principle according to which a pressure detection pipe measures average pressure according to the present invention.
Figure 6:
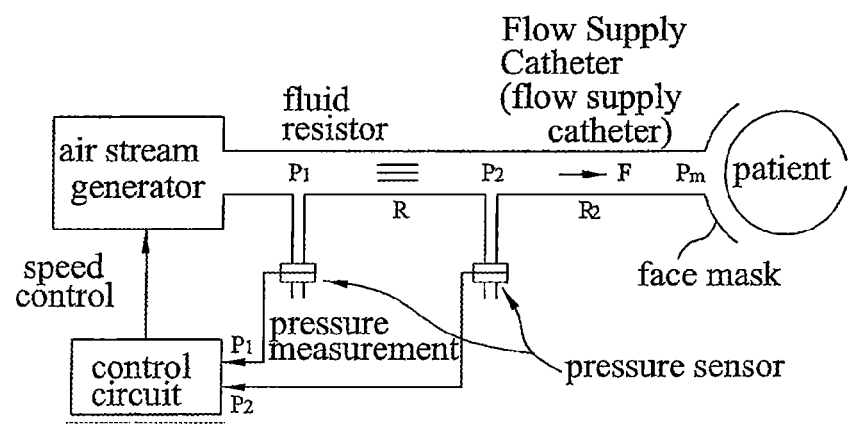
FIG. 6 is a block diagram schematically showing the construction of a conventional CPAP device.

FIG. 5 is a view showing a principle according to which the pressure detection pipe measures average pressure based on the present invention. In a case in which the pressure detection pipe is installed at the central portion of the flow supply catheter instead of being attached to the wall thereof, when a plurality of detection holes are formed, average pressure can be physically and substantially measured by using the structure of the pressure detection pipe that directly measures the pressure $P_m$ in the face mask.

That is, the pressures $P_1$ and $P_2$ are physically averaged in the pressure detection pipe and become average pressure $P_m$ expressed by an equation below.

$$P_m = \sum_{i=1}^{N} \frac{P_i}{N} \quad \text{Equation}$$

In Equation, N denotes the number of detection holes.

According to the prior art, since a technique of forming small holes at the wall of the flow supply catheter in order to measure pressure, installing a side tap (not shown) and connecting the pressure sensor to the tap is used, a pressure value at one point in the flow supply catheter is used as a representative value. However, according to the present invention, the thin pressure detection pipe is inserted into the flow supply catheter for air stream supply, the end portion of the pressure detection pipe is sealed, and two or more detection holes are formed at the outer circumferential surface of the pressure detection pipe, so that pressure values observed through the holes can be transferred to the pressure detection pipe and then can be physically and automatically averaged. Accordingly, the average value of the peripheral pressure values can be exactly measured.

In such a case, since the pressure detection pipe is inserted into the flow supply catheter, the air stream supply may be restricted by the sectional area of the pressure detection pipe. However, as the diameter of the detection pipe transferring pressure is small, the pressure can be quickly transferred.

Thus, if the diameter of the detection pipe is sufficiently small, the restriction of the air stream can be ignored. In addition, the amount of generated air stream is slightly increased, so that the amount of the air stream necessary for maintaining the positive pressure can be sufficiently obtained.

According to the present invention as described above, since only one control parameter $P_m$ is used, the control technique is very simple. Accordingly, the control circuit can be simplified and manufactured at low cost.

Since it is not necessary to assume that $R_c=0$ or to estimate $P_m$ from $P_1$ and $P_2$ as expressed by Equation 3 according to the prior art, very precise pressure control can be performed and thus the desired positive pressure can be precisely supplied.

Further, the pressure $P_m$ oscillated by the spontaneous breathing of a patient is directly measured, so that the breathing state of the patient can be easily detected.

Furthermore, only one pressure sensor is used, so that the manufacturing cost can be significantly reduced.

In addition, the thin pressure detection pipe is inserted into the flow supply catheter for air stream supply, the end portion of the pressure detection pipe is sealed, and two or more detection holes are formed at the outer circumferential surface of the pressure detection pipe, so that pressure values observed through the holes can be transferred to the pressure detection pipe and then can be physically averaged. Accordingly, the average value of the peripheral pressure values can be exactly measured.

Although the exemplary embodiments of the present invention have been described, it is understood that the present invention should not be limited to these exemplary embodiments but various changes and modifications can be made by one ordinary skilled in the art within the spirit and scope of the present invention as hereinafter claimed.

What is claimed is:

1. A CPAP (continuous positive airway pressure) device comprising:
    an air stream generator for generating positive pressure;
    a face mask connected to the air stream generator through a flow supply catheter;
    a pressure sensor measuring pressure in the face mask;
    a control circuit controlling the air stream generator; and
    a pressure detection pipe having a first side and a second side, the first side being installed such that a detection hole is located at a connection portion between the face mask and the flow supply catheter in order to directly measure pressure in the face mask, and the second side being connected to the pressure sensor through a through hole formed in the flow supply catheter,
    wherein the pressure sensor is connected to the second side of the pressure detection pipe to measure pressure of the detection hole formed at the first side of the pressure detection pipe and outputs the measured pressure value to the control circuit,
    the control circuit distinguishes average positive pressure from pressure caused by spontaneous breathing of patient according to values of the pressure in the face mask, which are input from the pressure sensor, and controls a speed of the air stream generator such that preset positive pressure is supplied to the patient, and
    the air stream generator generates air stream such that the pressure in the face mask maintains proper positive pressure under a control of the control circuit.

2. The CPAP device as claimed in claim 1, wherein the pressure detection pipe has a diameter smaller than a diameter of the flow supply catheter, an end portion of the pressure detection pipe adjacent to the face mask is sealed, the detection hole is formed in the pressure detection pipe vertically to air stream, and the pressure detection pipe is selectively fixed to a wall of the flow supply catheter or not.

3. The CPAP device as claimed in claim 2, wherein, when the pressure detection pipe is not fixed to the wall of the flow supply catheter, two to N detection holes are formed vertically to the air stream, and a peripheral pressure value, which is physically averaged, is measured in the pressure detection pipe, and, when the N detection holes are formed, an angle between two adjacent detection holes about a central axis of the pressure detection pipe is 360°/N when viewed in a sectional view.

4. The CPAP device as claimed in claim 1, wherein the control circuit controls the pressure in the face mask to a desired level by using a signal, which has a frequency lower than a breathing frequency and is obtained by low-pass filtering a continuous signal of the pressure measured by the pressure sensor, and detects only a breathing signal by high-pass filtering the continuous signal using a signal having a frequency higher than the breathing frequency.

* * * * *